United States Patent [19]

Jöbsis

[11] 4,223,680
[45] Sep. 23, 1980

[54] METHOD AND APPARATUS FOR MONITORING METABOLISM IN BODY ORGANS IN VIVO

[75] Inventor: Frans F. Jöbsis, Durham, N.C.

[73] Assignee: Duke University, Inc., Durham, N.C.

[21] Appl. No.: 17,727

[22] Filed: Mar. 5, 1979

Related U.S. Application Data

[63] Continuation-in-part of Ser. No. 810,777, Jun. 28, 1977.

[51] Int. Cl.² ............................................. A61B 5/00
[52] U.S. Cl. .................................................. 128/633
[58] Field of Search ............... 128/633, 634, 664, 665; 356/39, 43–45, 432

[56] References Cited

U.S. PATENT DOCUMENTS

| | | | |
|---|---|---|---|
| 3,463,142 | 8/1969 | Harte | 128/633 |
| 3,647,299 | 3/1972 | Lavallge | 128/633 |
| 3,811,777 | 5/1974 | Chance | 128/633 |
| 3,830,222 | 8/1974 | Chance | 128/633 |
| 3,998,550 | 12/1976 | Konishi et al. | 128/633 |
| 4,077,399 | 3/1978 | Leroy | 128/633 |
| 4,086,915 | 5/1978 | Kofsky et al. | 128/633 |

*Primary Examiner*—William E. Kamm
*Attorney, Agent, or Firm*—B. B. Olive

[57] ABSTRACT

A spectrophotometric method, apparatus and reflectance technique is directed to non-invasive, harmless, continuous, atraumatic, in vivo, in situ monitoring of metabolism in a body organ utilizing measuring and reference wavelengths within the near infrared region, i.e., 700–1300 nm. Monitoring of oxidative metabolism is accomplished by monitoring oxygen sufficiency in an organ, normally an internal vital organ, e.g., the brain or heart, of a living human or animal body. Advantage is taken of the critical characteristic of cellular enzyme cytochrome a, $a_3$ within the optical path and within the radiated portion of the selected organ from which the light so reflected for absorbing the selected measuring wavelength and for light of this measuring wavelength, as well as at least one reference wavelength within the same defined infrared region and at a low, non-hazardous level of intensity to travel to the organ, be reflected and be detectable at a point spaced from the point of entry and at the end of a relatively long path, e.g., of several centimeters length, which may include substantial content of bone as well as soft tissue. The method corrects for skin blood flow effects, variations in laser diode output and variations in metabolic and circulatory parameters during measuring.

30 Claims, 8 Drawing Figures

METHOD AND APPARATUS FOR MONITORING METABOLISM IN BODY ORGANS IN VIVO

The invention described herein was made in the course of work under a grant or award from the Department of Health, Education and Welfare.

This application represents a continuation in part of copending application Ser. No. 810,777, filed June 28, 1977, entitled "Method and Apparatus for Monitoring Metabolism in Body Organs", still pending.

BACKGROUND OF THE INVENTION

1. Field of the Invention

The invention pertains to a spectrophotometric reflectance method and apparatus for monitoring metabolism and is illustrated as monitoring cellular oxidative metabolism by conducting non-invasive, in vivo, harmless, continuous in situ measurements of changes in the steady state oxidation-reduction of cellular cytochromes together with changes in skin and bone blood volume, in organ blood volume, the oxygenation state of hemoglobin and the rate of blood flow in a vital organ such as the brain, heart or kidney, in other organs, in limbs or other parts of a living human or animal body.

2. History of the Prior Art

An extensive and useful history of the prior art is given in the referred-to copending application, Ser. No. 810,777 and which is deemed incorporated herein by reference to avoid repetition of the same.

As was pointed out in such description of the prior art, while circulatory-respiratory functions, arterial blood oxygenation and blood samples, per se, have been monitored by spectrophotometric techniques, presently existing methods are not suited for assessing the sufficiency of oxygen and metabolism in general in such vital organs as the brain and heart. Further, such prior methods do not provide precise information and are often traumatic as well. Consequently, an obvious need exists for a method by which this life sustaining parameter, i.e., cellular oxidative metabolism, can be measured in vivo, in situ and monitored continuously with precision and in a non-invasive, non-traumatic manner. Equally important is a need to be able to monitor blood volume and blood flow rate of the organ being monitored.

In order to distinguish and understand the invention of the present application, a summary of the invention of the copending application Ser. No. 810,777 is restated here for reference as what is regarded as the most pertinent prior art.

It is known that the cellular enzyme cytochrome a, $a_3$ (also known as cytochrome c oxidase) has a key role in oxidative metabolism. That is, it has been established that the enzyme interacts directly with oxygen and mediates the release of energy during the reduction of $O_2$ to $H_2O$. This is achieved by the catalytic donation of four electrons to $O_2$ and subsequent combination with four H+ ions. Under conditions of an inadequate $O_2$ supply, electrons accumulate and the enzyme population shifts to a more reduced steady state. Consequently, an ability to continuously measure and monitor the redox state of this oxygen utilizing enzyme in vivo, in situ would provide decisive information on the parameter of oxygen sufficiency in any tissue or organ in question. The invention of the copending application Ser. No. 810,777 provided that capability as well as the capability to monitor blood volume and blood flow rate in a manner which is non-invasive and atraumatic.

In the invention of the copending application Ser. No. 810,777, this was accomplished by optical techniques, the application of which was made possible by observing that the body and its organs are relatively pervious to low level, non-hazardous light energy in the near infrared region of the spectrum. Of particular importance, it was discovered that a beam of relatively low level, non-intense radiation in reference and measuring wavelengths of from about 700–1300 nm can penetrate, reach the organ and be detected and monitored at the end of a relatively long optical path in any selected portion of a human or animal body, which path includes bone as well as soft tissue. While such operating principles were illustrated in a manner indicating them to be useful in either a transillumination or a reflectance technique, emphasis was given in the invention of copending application Ser. No. 810,777 to a transillumination technique whereas in the present invention and application emphasis is given to use of the same basic principles in a reflectance technique.

By fortunate coincidence, cytochrome a, $a_3$ has radiation, absorption properties in the aforenoted spectral region, the character of which varies according to its oxidation state. Thus, the invention of the copending application recognized that it is possible to monitor the redox state of this oxygen utilizing enzyme by a spectrophotometric method not known to the art prior to the invention of the copending application.

The spectrophotometric measurements, according to the invention of the copending application were made in vivo by transmitting near infrared radiation in at least two different and periodically recurring wavelengths to the test organ, in situ, and detecting and measuring the radiation intensity which emerged for assessment of biochemical reactions utilizing the Beer-Lambert Law as referred to in the copending application. One of the wavelengths selected was in a range at which oxidized cytochrome a, $a_3$ is highly absorptive. One or two additional wavelengths outside the peak of the cytochrome absorption band, but preferably in relatively close proximity to the measuring wavelength were presented in sequence to provide one or more reference signals. A simple subtraction or ratio calculation between the measuring and reference signals was achieved by appropriate circuitry and the non-specific changes in the intensity of transmitted radiation not attributable to absorption by cytochrome a, $a_3$ were eliminated.

Although the capability for continuously monitoring cellular oxidative metabolism by monitoring the redox state of cytochrome a, $a_3$ in the cells of the selected organ was of principal interest to the invention of the copending application Ser. No. 810,777, ancillary data on circulatory parameters related to functioning of the organ was also shown to be obtainable. As an example, it was shown that the oxygenation state of the blood supplied to a given organ can be monitored by the hemoglobin band at slightly different wavelengths, e.g., 740–780 nm, in the aforenoted near infrared region of the spectrum. Likewise, data on the total blood volume of the organ was shown to be obtainable by monitoring a hemoglobin (Hb) oxyhemoglobin ($HbO_2$) isobestic point. This well-known spectrophotometric term refers to a wavelength at which two forms of the same molecule or mixture of molecules have equal absorption intensity. Thus, for oxygenated and disoxygenated hemoglobin, such a point was found to occur variously between 810 and 820 nm. This variation of stated wavelengths derives from problems arising from the very low optical densities of Hb and $HbO_2$ in this range and the relative insensitivity of most commonly available spectrophotometers in this wavelength range. In practice, any wavelength in the entire range of 815±5 nm was stated to be useful without jeopardy to the results in situations where the measurements are less sensitive to small errors. As further pointed out in the copending application, a yet wider range of wavelengths can serve the purpose since even small blood volume changes will outweigh the possible interference by $Hb \rightleftharpoons HbO_2$ shifts. In another approach described in the copending application, the less practiced technique of combining two wavelengths with opposite optical density (OD) responses to the interfering reaction can be combined. Thus, for $Hb \rightleftharpoons HbO_2$ equal $\Delta OD$ values but of opposite sign were shown to occur at 786 and 870 nm. This combination of signals of equal strength but opposite sign at two wavelengths is called a "contrabestic pair". It is especially useful when two reference wavelengths are used straddling the peak to be measured in conditions of intense and changing, wavelength dependent scattering. A series of wavelengths chosen such that the net sum of their optical density changes becomes zero is another method of practicing the cancellation of interfering reactions. In contradistinction, "equibestic" pairs can be used to correct for errors arising when the spectral effects of a Hb to $HbO_2$ shift or the reverse predominate. In the case of the invention of the copending application, a reference wavelength was selected which has an equal OD effect in the same direction as the one occurring at the measuring wavelength when the interfering reaction proceeds.

In addition, blood flow rates in the invention of the copending application were monitored, albeit discontinuously, by the rapid administration of a small quantity of a dye, e.g., "cardiogreen", having absorption properties in the near infrared spectral region or alternatively by having the test subject take single breaths of a gas mixture containing a high and low concentration of oxygen in alternating sequence or one breath of a mixture with a small, innocuous admixture of CO. By selecting two wavelengths for differentially measuring the optical density of the organ in the spectral region of the absorption band of the dye, an optical signal indicating the arrival and subsequent departure of the dye in the cerebral circulation and dilution in the total blood volume, the so-called transit time, was measured. The latter was stated in the copending application to be directly indicative of the rate of blood flow as proven by Zierler (see the book "PRINCIPLES OF APPLIED BIOMEDICAL INSTRUMENTATION"). Similarly, in the invention of the copending application, the optical density differences of the hemoglobin compounds ($HbO_2$, HbCO or other) were described as useful to provide the optical signal when the inspired air is suddenly and briefly varied. Having restated a summary of the invention of copending application Ser. No. 810,777, a summary of the present invention will be given.

SUMMARY OF THE INVENTION

Using the foregoing summary of the prior invention set forth in copending application Ser. No. 810,777 as a reference, it may be succinctly stated that the present invention is directed to a unique spectrophotometric reflectance method and apparatus for measuring oxidative metabolism utilizing the basic discoveries set forth with regard to the prior invention. As with the prior invention, the method of the present invention utilizes a beam of relatively low level, non-intense radiation in reference and measuring wavelengths of from about 700–1300 nm. As with the prior invention, the present invention provides an ability using a reflectance method to monitor cellular metabolism as a means of measuring local metabolism in a continuous, harmless, non-invasive manner. The spectrophotometric measurements, according to the present invention, are made by transmitting near-infrared radiation in at least two different and periodically recurring wavelengths to the test organ, in situ, and detecting and measuring the radiation intensity which emerges at a point spaced from the point of light entry for assessment of biochemical reaction utilizing the Beer-Lambert Law in the same manner as in the prior invention.

As disclosed in a specific embodiment, the present invention is shown applied to the measurement of oxygen sufficiency in the brain. The light source and light detector are spaced apart on the same side of the head. The method provides for detecting light reflected back to the light source location and using this as a correction for skin blood volume changes. The method also provides for discriminating between light scattered by the gray matter and reflected from the white matter of the brain and providing a signal known to be indicative of the oxygen sufficiency in the gray matter of the brain.

While the prior invention of copending application Ser. No. 810,777 met all of its expectations, the method of the present invention as compared to the method of the prior invention has the advantage of requiring less complexity in the equipment and also should be expected for many applications to provide better localization of the area from which signals are obtained. Thus, while the method of the prior invention is expected to maintain its usefulness for many of the numerous applications for measuring local metabolism in the living human body, the present invention is likewise expected to exhibit special advantages in other applications such as measuring oxidative metabolism in the living human brain in a manner not heretofore accomplished.

DETAILED DESCRIPTION OF THE INVENTION

A salient feature of the present invention, as with the invention of copending application Ser. No. 810,777, is the observation that light energy in the near infrared region having wavelengths in the range of from about 700–1300 nm and at a relatively low, non-hazardous intensity can be made to penetrate and be reflected and scattered from both soft tissue and bone surrounding a living organ as well as penetrate and be reflected and scattered from the organ itself and in relatively long optical paths and the detected light at the end of the paths can be collected and related to oxidative metabolism. This wavelength range has also been proven critical since within the 700 to 1300 nm wavelength range oxygenated hemoglobin ($HbO_2$) has extremely low absorption characteristics, whereas deoxygenated hemoglobin (Hb) displays some weak absorption which slowly rises with decreasing wavelengths below 815 nm to a small peak in absorption around 760 nm. Because of these optical properties, the Hb-$HbO_2$ steady state (i.e., the venous-arterial average) can be monitored.

In addition and of significant importance, the present invention recognizes that cytochrome a, $a_3$ in living body tissue also exhibits an oxygen dependent absorption band in the 700 to 1300 nm wavelength range of the spectrum. When this key enzyme in oxidative reactions is in the presence of sufficient oxygen, a weak absorption band exists in the 780 to 870 region with a maximum at a wavelength of about 820 to 840 nm. The absence of oxygen results in a complete reduction of the enzyme and a concomitant disappearance of the absorption band. The present invention provides a spectrophotometric reflectance method by which this characteristic may be monitored to monitor oxygen sufficiency in the enzyme.

Cytochrome a, $a_3$ is the terminal member of the mitochrondrial respiratory chain and functions as a donor of four electrons to molecular oxygen in the final step of the main pathway of oxidative metabolism in the cells. In this reaction, the electrons are transferred to oxygen from the four metallic redox components of the enzyme, the two iron atoms of the a and $a_3$ hemes and two copper atoms. Subsequent or concomitant combination with four hydrogen ions leads to the formation of $H_2O$. The free energy difference between the hydrogens in the metabolic substrates and in $H_2O$ is partially conserved in the form of high energy phosphate bonds through the oxidative phosphorylation of adenosine diphosphate (ADP) to adenosine triphosphate (ATP). The latter compound serves as the primary free energy carrier in the cell and meets the free energy needs of most of the endergonic reactions required for normal physiological function and cell survival. Since better than 90 percent of cellular ATP production is by means of oxidative phosphorylation and since oxygen utilization is ultimately governed by the rate of transfer of electrons to oxygen from cytochrome a, $a_3$, this enzyme performs a critical role in cellular oxidative metabolism and energetics. In the absence of sufficient $O_2$, electrons accumulate in cytochrome a, $a_3$, producing a more reduced steady state. Thus, the invention recognizes that direct measurements on the redox state of this enzyme will provide conclusive data on the adequacy of oxygen availability and its utilization in living tissue and organs. The spectrophotometric reflectance method of the present invention provides a method for obtaining such measurements.

In carrying out a continuous, non-invasive, in vivo, in situ monitoring of the redox state of cytochrome a, $a_3$, near-infrared radiation of appropriate wavelengths and at a relatively low power level and corresponding relatively low density is presented at one site and is transmitted to and reflected from the organ under investigation, and the reflected and scattered light emerging from laterally-spaced exit is conducted to a photomultiplier tube or other photodetector for detection and measurement.

The monitoring, as in the prior invention, may be conducted in either a dual or triple wavelength mode with one of the wavelengths being selected to provide a measuring signal and the others a reference signal as illustrated in the copending application Ser. No. 810,777. The measuring wavelength is preferably at about 840 nm, the center of the cytochrome a, $a_3$ absorption peak observed in vivo, but the choice is not so limited since other wavelengths in the absorption band can be utilized.

By calculating the difference between the measuring and reference signals, the non-specific changes in the reflectance characteristics not attributable to cytochrome absorption are in effect cancelled out. Appropriate electronic circuits may be used to amplify and demodulate the separate signals, convert them to DC current and subtract them for a differential recording in the manner set forth in the prior copending application.

In one version of the dual mode, the isobestic point of Hb-$HbO_2$ at 815 nm$\pm$5 nm is used as the reference wavelength with a feedback control on the signal produced to compensate for changes in blood volume. That is, a negative feedback circuit, for example, connected to the high voltage source which supplies the photomultiplier tube is used to compensate the reference signal for changes in the reference signal level caused by blood volume changes in the tissue being monitored. The voltage adjustment is then maintained in the subsequent interval when the measuring wavelength is transmitted. Since the changes in voltage supplied to the photomultiplier are directly proportional in magnitude to the changes in blood volume over the optical path, in effect they measure this important circulatory parameter and are recorded.

In the triple wavelength mode, three wavelengths are presented, i.e., the measuring wavelength and two reference wavelengths. Desirably, the reference wavelengths straddle the measuring wavelength and are in relatively close proximity to it. A suitable choice would be for one reference wavelength to be about or less than, say, 75 nm lower than the measuring wavelength and the other to be about or less than 75 nm higher. When interference by blood volume changes is present, resort is made to a contrabestic pair for the two reference wavelengths. When Hb$\rightleftharpoons HbO_2$ changes predominate over blood volume changes an equibestic pair is employed.

As has been noted supra, hemoglobin also possesses oxygen dependent absorption properties in the near-infrared region of the spectrum which permits continuous monitoring of the Hb-HbO$_2$ steady state. In practice, advantage is taken of the fact that deoxygenated hemoglobin (Hb) exhibits a relatively weak absorption which slowly rises with decreasing wavelengths below 815 nm to a small peak in the vicinity of about 760 nm. Thus, determinations on the Hb-HbO$_2$ steady state can be made by differential measurements at wavelengths of about 760 nm to 815 nm, with the 815 nm wavelength (Hb-HbO$_2$ isobestic point) serving to provide the reference signal.

As can be seen from the immediately foregoing description, the spectrophotometric reflectance method of the present invention is adapted to utilize the discoveries and measuring techniques of the prior invention. The description now turns to pointing out the more distinctive features of the present invention as compared to the prior invention. To illustrate this comparison, the drawings are directed to application of the method of the present invention to measuring local metabolism in the brain of a living human or animal specimen, i.e., in vivo, harmlessly, non-invasively, continuously and rapidly.

Figure 1:
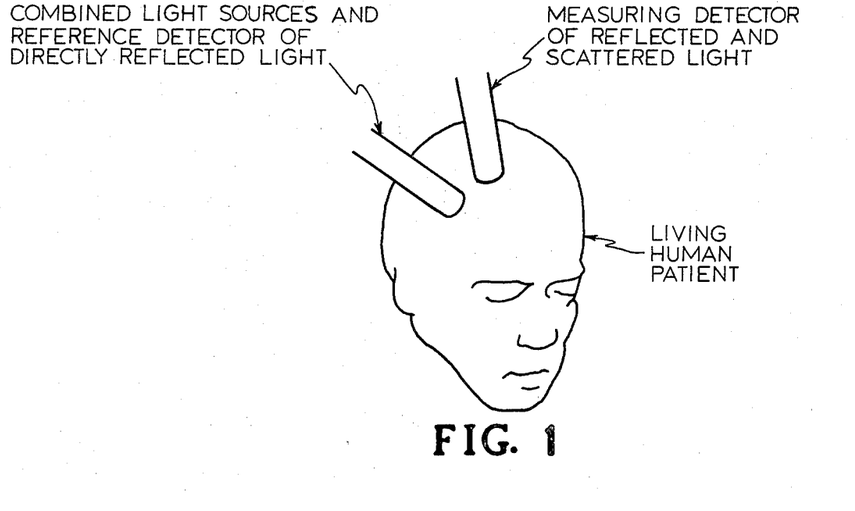
FIG. 1 is intended to represent the head of a living human patient and illustrating the general method of the invention.
Figure 2:
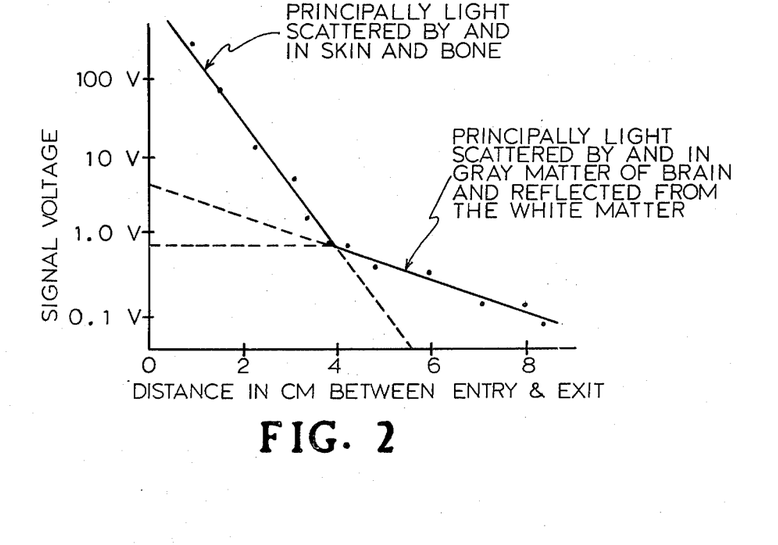
FIG. 2 is a plot of the relation of the distance between light entry and exit locations to the signal voltage and the source of the measured light.
Figure 3:
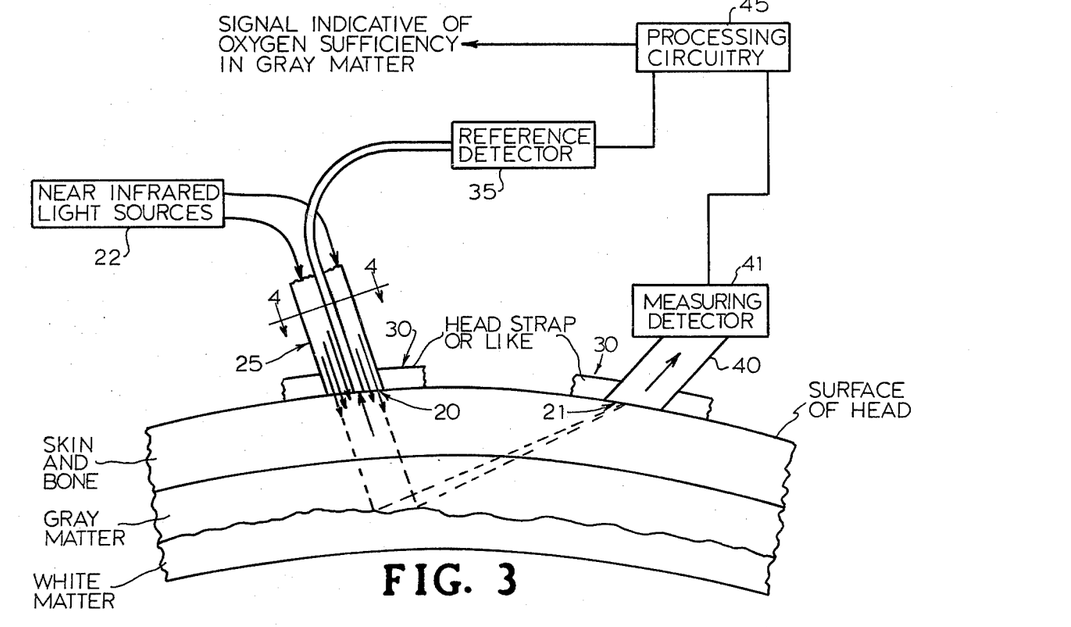
FIG. 3 diagrammatically illustrates the general method of the invention as applied to the head of a human or animal, in vivo.
Figure 4:
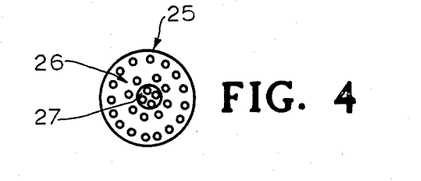
FIG. 4 represents a cross section through the combined light source and reference detector bundle.

As schematically illustrated in FIGS. 1, 3 and 4, two spaced-apart locations are chosen, one of which is designated as a point of light entry 20 and the other of which is designated as a point of light exit 21. Advantageously, any bare or bald skin area of sufficient size (1 cm$^2$ approximately) can be used as an entry or exit site without preparation. As will later be explained in reference to FIG. 2, the spacing between the light entry point 20 and light exit point 21 is critical for purposes of the invention and particularly so in reference to utilizing the invention in the manner described for measuring local metabolism in the brain of a living human.

An appropriate source of light 22 provides light within the near-infrared region of 700–1300 nm spectral range. Light from light source 22 is transmitted to the light entry location 20 through a fiber optics bundle assembly 25 having an outer annular fiber bundle assembly 26 surrounding an inner central smaller bundle assembly 27. The proximal end of the assembly 25 being located in a tightly pressed position against the light entry location 20 and secured by a suitable head strap 30 or other suitable mounting means so as to minimize leakage and loss of light at the point of entry. The general concentric arrangement of the outer annular fiber optics bundle 26 and central fiber optics bundle 27 are shown in the cross section drawing illustrated in FIG. 4. The outer bundle 26 will be noted as providing a means for transmitting infrared light within the designated spectral range to the point of light entry 20 so as to provide photons capable of penetrating both the skin and bone layer as well as the gray matter and white matter schematically illustrated in FIG. 3. Those photons which are directly reflected upwardly from tissues below the light entry assembly 25 or within a few millimeters of that point of entry are transmitted through the inner optic bundle 27 to an appropriate reference detector 35 whereas other photons are transmitted, reflected and scattered through and by the skin and bone structure, through and by the gray matter to and from the white matter to provide a continuous number of such photons reaching the point of light exit 21 where they are picked up by another single fiber optics bundle 40 and transmitted to a measuring detector 41, with the output of reference detector 35 and measuring detector 41 being directed to suitable processing circuitry 45 for conversion to a signal indicative of oxygen sufficiency in the gray matter as hereafter more fully described.

Since the types of light sources, reference detecting, measuring detecting and processing circuitry have already been fully described in the prior copending application Ser. No. 810,777, no attempt will be made here to describe the circuitry in anymore detail since the same should be readily apparent to those skilled in the art from the information already given.

What is of particular importance to the present invention is recognition of the discovery that the spacing between the points of light entry and exit 20, 21 has a significant relation to the source of photons which are picked up through the fiber optics bundle 40 and transferred to the measuring detector 41. For example, it will be seen that when the distance between the points of light entry and exit 20, 21 is less than approximately 4.25 centimeters that the photons reaching the exit point 21 will consist of light principally made up of photons scattered by and in the skin and bone. In contrast, it will be noted in reference to FIG. 2 that when the spacing between the points of light entry and exit 20, 21 is greater than approximately 4.25 centimeters that the photons reaching the fiber optics bundle assembly 40 will consist principally of light scattered by and in the gray matter of the brain. Thus, by using the inner fiber optic bundle 27 to receive light directly reflected and scattered upwards, photons reflected from the skin and bone will predominate as indicated in FIGS. 2 and 3 and using this as a reference to measuring detector 41 in processing circuitry 45, a signal can be obtained which is sufficiently accurate to represent oxygen sufficiency in the gray matter. Further, the photons representing those which have been scattered and reflected by the skin and bone and detected by reference detector 35 may be used for signal stabilization against variations in light output of source 22 and, importantly, for correction for skin blood volume changes.

In one embodiment of the invention, four legs of a five-legged fiber bundle were employed as the fiber bundle 26 to bring light of four wavelengths from the light source 22, comprising laser diodes, to the point of light entry 20. In the same fiber optics assembly 25, the fifth fiber bundle leg was employed to pick up the skin and bone reflectance in the area immediately adjacent to the entry point 20 of the laser light from light source 22. The same embodiment included appropriate subtraction circuitry for correction of blood volume changes attributable to the skin and bone. The sensors employed in reference detector 35 and measuring detector 41 were closely matched and associated with differential circuit means in the processing circuitry 45. Thus, one sensor was employed for measuring the light emanating from the head at the exit point 21 several centimeters away from the entry point 20. The second sensor 35 was employed for sensing the light reflected below the point of entry 20 and utilizing the appropriate processing circuitry 45 provided a useful signal indicative of oxygen sufficiency in the gray matter and corrected for changes in skin and bone blood volume. Further, the light from light source 22 was presented at measuring and contrabestic reference wavelengths alternately at a rate sufficiently rapid to provide a sufficiently short reference and measuring cycle such that the metabolic and circulatory parameters were treated as being essentially constant within the time period of each measuring cycle.

Figure 5:
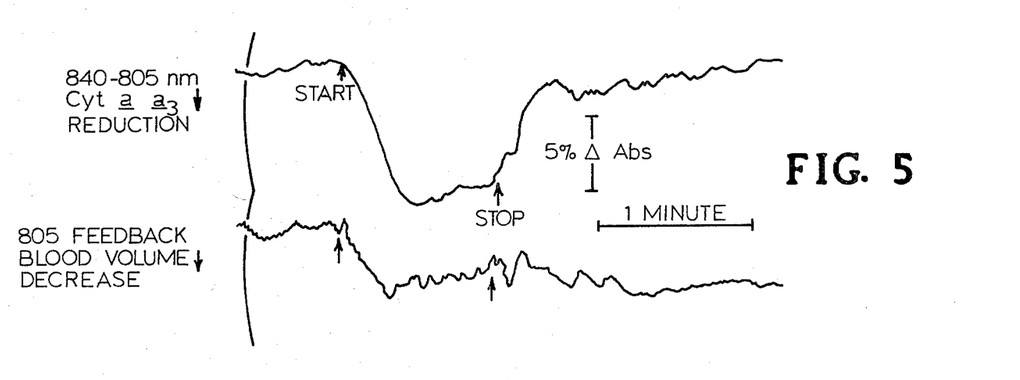
FIG. 5 is a representation of the reduction of $Cu_L$ of cytochrome a, $a_3$ and decrease of intracranial blood volume during one minute of hyperventilation, the illustrated cytochrome response being deemed fairly typical while the return of the blood volume trace is more variable but often returns more rapidly to the baseline than illustrated.
Figure 6:
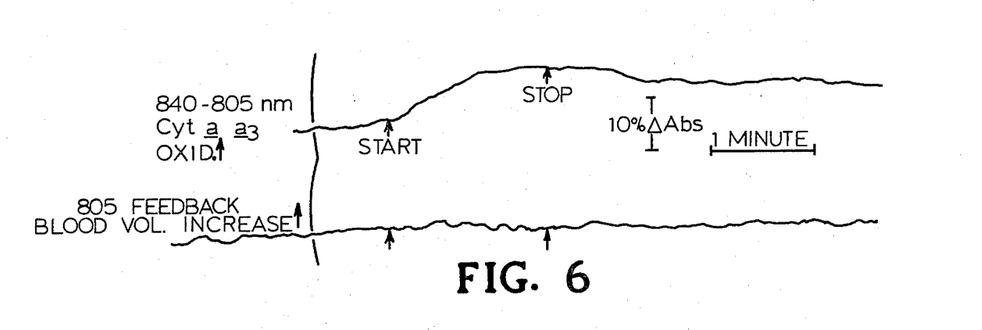
FIG. 6 illustrates the effect of hypercapnia plus hyperoxia produced by breathing 5% $CO_2$ plus 95% $O_2$ for 90 seconds. Here it should be noted that a long term increase of the base line, as shown, is often recorded after the first episode. The effects of the second and later exposures to the gas mixture tend to be superimposed on this new baseline.
Figure 6A:
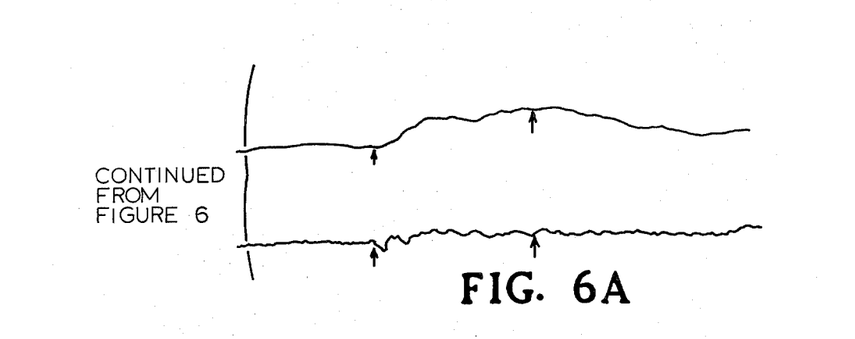
FIG. 6A represents a continuation of FIG. 6.

Data from actual experiments utilizing the present invention are illustrated in reference to FIGS. 5, 6 and 6A with FIG. 6A being a continuation of FIG. 6. The interpretation of these figures will be readily understood using the disclosure of the prior copending application Ser. No. 810,777 as background. In particular, FIG. 5 illustrates that hyperventilation, as in the prior invention, produces in the present invention the expected blood volume decrease and reduction of the $Cu_L$ atom of cytochrome a, $a_3$. Further, as illustrated in FIGS. 6 and 6A, ventilation with 95% $O_2$ plus 5% $CO_2$ produces an increased oxidation of cytochrome a, $a_3$ but only a small effect on the blood volume. This latter observation is not yet fully understood but it is to be noted that the 5% $CO_2$ by itself does produce a more noticeable increase in blood volume. Opposing influences of hyperoxia and hypercapnia are suspected to offset each other.

It is apparent from the above discussion that the spectrophotometric reflectance method of this invention, as with the prior invention, provides a capability for in vivo, in situ, non-invasive, atraumatic and continuous monitoring of three parameters of crucial significance related to organ metabolism and particularly in situations where information on the state of circulatory adequacy and oxygen sufficiency are needed. These parameters include:

1. The adequacy of oxygen availability for normal function of cytochrome a, $a_3$, the cellular enzyme which mediates better than 90 percent of the oxygen consumed in living tissue;
2. The total blood volume in the tissue under question; and
3. The steady-state status of the relative predominance of oxygenated arterial blood ($HbO_2$) and deoxygenated venous blood (Hb).

Additionally, it should be noted that blood flow rate may be monitored as previously set forth in the referred-to copending application and related to the parameters mentioned. While monitoring of the enumerated three parameters may constitute separate methods of monitoring, the invention contemplates monitoring of plural parameters.

In one embodiment, all three parameters are continuously monitored in a single system by a triple wavelength technique in which one reference and two measuring wavelengths are alternately presented to the tissue being tested at a rate (>30 Hz) providing sufficient time resolution for the monitoring of the most rapid metabolic reactions. An isobestic point of Hb-$HbO_2$ at a wavelength of 815 nm ±5 nm is used to provide the reference signal that is subtracted from the measuring signals. One of the measuring wavelengths monitors the oxidized cytochrome a, $a_3$ peak at about 840 nm while the other provides a signal on the Hb-$HbO_2$ steady state by monitoring the deoxygenated hemoglobin absorption peak at around 760 nm. The choice of measuring wavelengths is not limited to 760 and 840 nm, since other wavelengths in the cytochrome a, $a_3$ and hemoglobin absorption bands are likewise applicable. However, wavelengths at about 760 and 840 nm are generally preferred. The feedback control on the reference signal compensates for blood volume changes and is used to monitor blood volume in the test tissue in the organ. That is, as previously explained, voltage changes in the feedback loop are recorded as measure of changes in blood volume.

Figure 7:
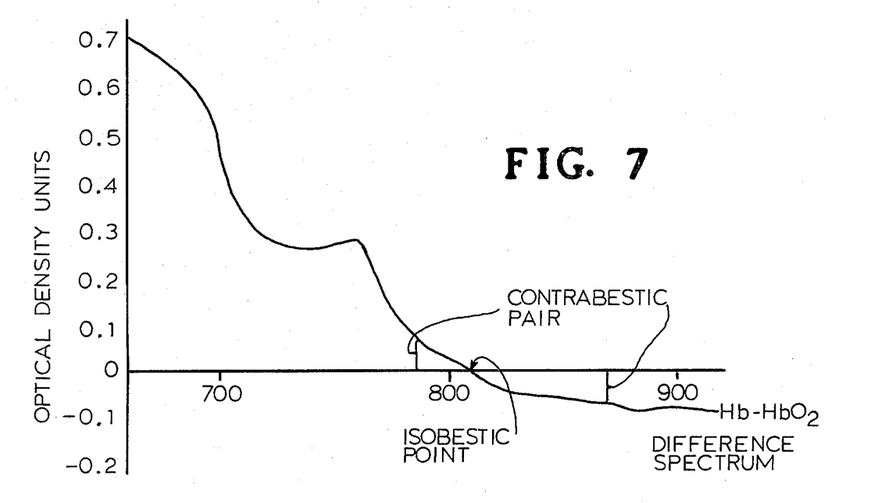
FIG. 7 shows the spectral differences observed when blood changes from $HbO_2$ to Hb and indicates a contrabestic pair from which blood volume changes as well as oxygenation changes may be determined according to the method of the invention.

In another, preferred embodiment, one wavelength at about 840 nm is used again for the measurement of the absorption band of oxidized cytochrome a, $a_3$ but the signals obtained from two wavelengths constituting a contrabestic pair in the hemoglobin spectrum are summed to provide correction for and measurement of changes in blood volume in the organ being tested, in the same manner as explained supra for a single Hb-$HbO_2$ isobestic wavelength. In addition, as shown in FIG. 7 which compares to FIG. 4C of the prior invention set forth in the copending application Ser. No. 810,777, the mathematical difference between absorption changes at the two contrabestic wavelengths is indicative of shifts in the Hb-$HbO_2$ steady state in the organ produced either by changes in the $O_2$ supply to the organ or by changes or malfunction of its metabolism. Thus, the use of a contrabestic pair of wavelengths straddling the measuring wavelength provides not only a better correction of the cytochrome a, $a_3$ signal during the occurrence of blood volume and light scattering changes but simultaneously provides information on shifts in the hemoglobin oxygenation of the blood in the test organ.

As previously noted, in respect to the prior invention the rate of blood flow through a given organ may also be measured by the method of this invention. The 815 nm feedback signal can be used as a measuring signal, or alternatively, the signal obtained by presenting light of a wavelength in the range where hemoglobin has a more intense absorption such as between 740–780 nm. One technique has used arterial injection of a bolus of dye having absorption properties in the selected test wavelength. The time taken for the bolus to pass through the optical pathway is then used to calculate blood flow rate by the so-called transit time technique. In a more preferred variation of the procedure, the test subject inhales a single breath of air containing a small admixture of carbon monoxide. The period of time in which the optical signal is affected by the presence in the blood of the first and highest concentration of the hemoglobin-carbon monoxide compound passing through the optical pathway is evident from a decrease in optical density arising from the face that the Hb-CO compound exhibits practically no light absorption properties in the near-infrared range. The temporary decrease in optical density is used to calculate the blood flow rate by recording intensity and time interval as described in the Zierler reference.

What the invention recognizes and what should be fully appreciated in the foregoing description is that the success of cerebral IR monitoring of oxygen sufficiency according to the invention depends upon the rate of oxidative metabolism and concomitantly the cytochrome content of extra cerebral tissues being very low in comparison with those of cerebral tissue. Because of this low concentration of cytochrome a, $a_3$ in skin and bone tissue and the short optical pathlength compared to the high cerebral cytochrome a, $a_3$ concentration and the long optical pathlength through the human brain, the total cytochrome a, $a_3$ signal upon transcranial exposure to the light derives predominantly (better than 98%) from brain tissue. The same holds true for the distribution of the total volume of blood. Although the concentration of cytochrome a, $a_3$ in heart muscle is much higher yet, the relative optical path lengths involved in the reflectance technique of the invention through non-myocardial and myocardial tissue within the chest produces a ratio of the same order of magnitude. Thus, a wide range of applications to monitoring of body organ metabolism generally, cellular metabolism and particularly cellular oxidative metabolism are suggested.

In addition to the naturally occurring compounds discussed so far, hemoglobin and cytochrome a, $a_3$, any other compound absorbing differentially in the near IR, depending on the metabolic or physiological function of the tissue, can be used as in the prior invention for monitoring purpose of such fractions. These other compounds may be either as yet unidentified naturally occurring ones or ones artificially introduced by ingestion or other administration. For one example, the use of indicator dyes having differential optical properties depending on the local pH is foreseen as a useful further application and extension of the technique since during $O_2$ deficiency the degradation of glucose to lactic acid (glycolysis) occurs and produces considerable shifts in tissue pH.

The present invention could also be used to great advantage in any clinical situation where the oxygen sufficiency of the brain, heart, or other organs, needs to be continuously monitored and studied. For example, such information is often of critical importance in the course of surgical operations, during treatment of patients in intensive care units and especially in the case of premature babies as has been previously recognized and discussed in U.S. Pat. No. 3,704,706. In the latter situation, the critical question is how much oxygen to give the premature baby. Too much can result in blindness and permanent lung damage, while too little ends in brain damage or death. Improvements in monitoring oxygen levels, such as provided by this invention, can greatly reduce these problems.

In summary, there has been disclosed what is believed to be a basically new approach to monitoring cellular metabolism in a living organ and more specifically to monitoring cellular oxidative metabolism in vivo, in situ, non-invasively and continuously in a manner not heretofore accomplished and productive of much useful information for the health of the patient. Those skilled in the art will also appreciate the forms of display available for the information of interest such as by recorder, oscilloscope, tape, printer, or the like.

By the terms "organ metabolism", "cellular metabolism", "cellular oxidative metabolism", "metabolic activity", and the like, as used herein and in the appended claims as being "information" of interest, there is meant the sum of all physical and chemical processes by which energy is made available for use by the organ. Circulatory processes by which the required metabolities are transported to cellular reaction sites are deemed to be included in such terminology as well as the metabolic reactions within the cells of the organ. The broad concept of examining with one measuring wavelength a cellular activity, e.g., cytochrome a, $a_3$ oxidation, related to a transmission characteristic of such wavelength and the same activity with at least one other reference wavelength of different characteristic and comparing the respective reflected wavelength intensities as a difference or ratio as a measure of such activity, it is believed will hereafter suggest many as yet unpredictable applications of such concept.

Of particular value in the application of the invention is that unlike hazardous surgical laser apparatus and the like, the method and apparatus of the invention operates well below hazardous light levels known to cause thermal, photochemical or other damaging tissue reactions. The accepted laser safety standard (American National Standard 136.1-1976) for the near-infrared range allows a Maximum Permissible Exposure (MPE) for skin exposure to a laser beam of 100 milliwatts per square centimeter average power for multiple pulse exposure periods longer than 10 seconds. As a comparison, the presently performed experiments have not employed more than 15 milliwatts per square centimeter time average power, i.e., approximately 6 times less than the MPE. Most experiments, however, have been performed with substantially less intensities, i.e., approximately 35 times less than the MPE.

What is claimed is:

1. A spectrophotometric reflectance method for measuring local metabolism of a body organ such as the brain, in situ, in vivo, non-invasively, atraumatically, harmlessly, rapidly and continuously, said method comprising the steps:

(a) locating and fixing the body in a position appropriate to the measuring operation;

(b) selecting an optical transmission-reflectance path including said organ and extending for several centimeters between points of light entry and exit said points of light entry and exit being laterally spaced several centimeters apart and positioned on contiguous skin surface areas of the body;

(c) establishing a plurality of near-infrared light sources located external of the body and having light emissions of different wavelengths in the 700 to 1300 nanometer spectral range and of an intensity below the level damaging to the body and said organ but sufficient to be detectable by a light sensor after transmission through any skin, bone and tissue included in said path and scattering in and reflectance from said organ along said path, said emissions including at least one measuring wavelength and at least one reference wavelength within said spectral range, each said measuring wavelength being selected such that said organ exhibits a selective absorption therefor, the extent of which is dependent upon a specific state of metabolic activity of said organ;

(d) directing said light emissions at said measuring and reference wavelengths sequentially at said point of entry to be transmitted, reflected and scattered along said path and to said organ and receiving the light emissions reflected directly back from said skin, bone and tissue at or within a few millimeters of said point of entry as well as the light emissions reflected and scattered from said organ at a point several centimeters away from said point of entry and light sensor and circuit means adapted to produce and electrical output signal corrected for changes in blood volume of said skin, bone and tissue during the measuring cycle and representing the difference in absorption of said measuring and reference wavelengths by the organ as a function of the state of said metabolic activity; and (e) converting said electrical output signal to a signal providing a substantially continuous and rapid measure of said activity.

2. The method of claim 1 wherein said organ is the brain.

3. The method of claim 1 including the step of receiving said light emissions reflected back from said skin, bone and tissue at said point of entry in light receptor means structurally combined with light transmission means connected to said light sources and removably secured to the body at said point of entry.

4. The method of claim 1 including the step of utilizing said light emissions reflected back from said skin, bone and tissue to correct for variations in output of said light sources during said measuring operation.

5. The method of claim 1 wherein said organ comprises the brain, said points of light entry and exit comprise spaced points on the head of the body having the brain organ being measured and including the step of sensing and electrically processing said light emissions reflected back at said point of entry in a manner enabling reflected and scattered light received at said exit point mainly from the skin and bone of the head to be discriminated from reflected and scattered light received at said more distant exit point from the gray and white matter of the brain whereby in said processing said signal is developed as indicative of oxygen sufficiency in said gray matter.

6. The method of claim 1 including at least two reference wavelengths comprising a contrabestic pair and processing the sum of the absorption changes at the two contrabestic wavelengths to produce a signal indicative of blood volume changes and using the difference of the absorption changes in said wavelengths to produce a signal indicative of changes in oxygenation of the blood in said organ.

7. The method of claim 1 wherein each respective said measuring wavelength is selected within an absorption band of a metabolite, enzyme or other cellular biochemical entity controlling said state of activity and wherein each said reference wavelength to which a respective measuring wavelength is referred is selected so as to be more distant from the peak of the respective said band within which such respective wavelength resides.

8. The method of claim 1 wherein said activity is one of cellular metabolism.

9. The method of claim 8 wherein said activity is that of the redox state of enzyme cytochrome a, $a_3$.

10. The method of claim 8 wherein said activity is that of hemoglobin oxygenation in said organ.

11. The method of claim 1 wherein said activity relates to local changes in blood volume in said organ.

12. The method of claim 1 including the step of periodically interrupting normal measuring of said metabolism by admitting an agent to said body in a manner enabling such agent to reach said organ and designed to effect a fluctuating change of the absorption properties within said organ over a period of time effecting a corresponding change in said electrical output signal during such time, and recording the intensity of said fluctuating change and the time interval between the beginning and end of said change in the output signal brought about by said agent within said organ as a measure of the blood flow rate to said organ.

13. The method of claim 12 wherein said agent comprises a dye agent.

14. The method of claim 12 wherein said agent comprises a gaseous agent.

15. The method of claim 1 wherein said activity is that of the redox state of enzyme cytochrome a, $a_3$ in said organ.

16. The method of claim 1 wherein said activity is that of hemoglobin oxygenation in said organ.

17. The method of claim 1 including at least two said reference wavelengths comprising a contrabestic pair or series.

18. A spectrophotometric reflectance apparatus for measuring in situ, in vivo, non-invasively, atraumatically, harmlessly, rapidly and continuously a local metabolic, oxygen dependent activity of a body organ such as the brain of a body where such activity bears a measurable relation to an oxygen dependent absorption characteristic of the organ for a particular wavelength of light transmitted therethrough, comprising:

(a) light source means including:
  (i) a plurality of near-infrared light sources located external of the body and having light emissions of different wavelengths in the 700 to 1300 nanometer spectral range and of an intensity below the level damaging to the body and said organ but sufficient to be detectable by a light sensor after transmission through any skin, bone and tissue included in an optical transmission-reflectance path including said organ and extending for several centimeters between points of light entry and exit laterally spaced several centimeters apart and located on contiguous skin surface areas of the body and after scattering in and reflectance from said organ along said path, said emissions including at least one measuring wavelength and at least one reference wavelength within said spectral range, each said measuring wavelength being selected such that said organ exhibits a selective absorption therefor, the extent of which is dependent upon a specific state of a local metabolic, oxygen dependent activity of said organ;
  (ii) means operatively associated with said light sources to produce emissions representing at least one said measuring wavelength and at least one said reference wavelength within said spectral range for transmission along said path to said organ and at levels of intensity below that which would be damaging to the body and said organ; and
  (iii) light transmission means for receiving, transmitting and directing the output light emissions of said light sources at said measuring and reference wavelengths to a selected fixed light entry point on said body to be transmitted, reflected and scattered along said path and to said organ;

(b) first detector means fixed to said body proximate said entry point for receiving and transmitting the light emissions reflected directly back from said skin, bone and tissue at or within a few millimeters of said point of entry;

(c) second detector means fixed to said body at a fixed light exit point on said body and spaced several centimeters away from said fixed light entry point for receiving and transmitting the light emissions reflected and scattered from said organ;

(d) light sensor and circuit means connected to receive the light emission outputs of said first and second detector means and adapted to produce an electrical output signal corrected for changes in blood volume of said skin, bone and tissue during the measuring cycle and representing the difference in absorption of said measuring and reference wavelengths by the organ as a function of the state of said local metabolic oxygen dependent activity; and (e) means for converting said electrical output signal to a signal providing a substantially continuous and rapid measure of said activity.

19. The apparatus of claim 18 wherein said means operatively associated with said light sources comprises means for sequentially operating said light sources.

20. The apparatus of claim 18 wherein said light transmission and first detector means are structurally combined and removably secured to the body at said point of entry.

21. The apparatus of claim 18 wherein said light sensor and circuit means include means for utilizing said light emissions reflected back from said skin, bone and tissue at said point of entry to correct for variations in output of said light sources during said measuring operation.

22. The apparatus of claim 18 wherein said organ comprises the brain in the head of said body, said points of light entry and exit comprise spaced points on the head and wherein said light sensor and circuit means include means adapted for sensing and electrically processing said light emissions reflected back at said point of entry in a manner enabling reflected and scattered light received at said exit point mainly from the skin, bone and tissue of the head to be discriminated from reflected and scattered light received at said more distant exit point from the gray and white matter of the brain whereby in said processing said signal is developed as indicative of oxygen sufficiency in said gray matter.

23. The apparatus of claim 18 wherein said light sources and said means for sequentially operating said light sources produce at least two reference wavelengths comprising a contrabestic pair and said light sensor and circuit means are adapted for processing the sum of the absorption changes at the two contrabestic wavelengths to produce a signal indicative of blood volume changes and being further adapted for using the difference of the absorption changes in said wavelengths to produce a signal indicative of changes in oxygenation of the blood in said organ.

24. The apparatus of claim 18 wherein said activity is one of cellular metabolism and said wavelengths operate in reference thereto.

25. The apparatus of claim 18 wherein said activity is one of cellular oxidative metabolism and said wavelengths operate in reference thereto.

26. The apparatus of claim 18 wherein said activity is that of the redox state of enzyme cytochrome a, $a_3$ and said wavelengths operate in reference thereto.

27. The apparatus of claim 18 wherein said activity is that of hemoglobin oxygenation in said organ and said wavelengths operate in reference thereto.

28. The apparatus of claim 18 wherein said activity is that of local changes in blood volume in said organ, including means for establishing a feedback voltage to maintain at some predetermined level the said reference signal corresponding to a selected said reference wavelength and monitoring said voltage as a measure of said volume.

29. The apparatus of claim 18 wherein said measured activity is that of the redox state of enzyme cytochrome a, $a_3$ in said organ.

30. The apparatus of claim 18 wherein said light sources and means for operating said light sources are adapted to produce a pair of said reference wavelengths comprising a contrabestic pair.

* * * * *

UNITED STATES PATENT AND TRADEMARK OFFICE
CERTIFICATE OF CORRECTION

PATENT NO. : 4,223,680
DATED : Sept. 23, 1980
INVENTOR(S): Frans F. Jöbsis

It is certified that error appears in the above—identified patent and that said Letters Patent is hereby corrected as shown below:

Col. 9, line 29, "cytrochrome" should be --cytochrome--.

Col. 10, line 43, "face" should be --fact--.

Col. 11, line 10, "fractions" should be --functions--.

Signed and Sealed this

Twenty-eighth Day of July 1981

[SEAL]

Attest:

Attesting Officer

GERALD J. MOSSINGHOFF

Commissioner of Patents and Trademarks